United States Patent [19]

Luethi et al.

[11] 4,228,814
[45] Oct. 21, 1980

[54] CLEANING APPARATUS FOR TEST ELECTRODES

[75] Inventors: Peter Luethi, Uster; Werner Steinmetz, Wetkizon, both of Switzerland

[73] Assignee: Zellweger Ltd., Switzerland

[21] Appl. No.: 945,395

[22] Filed: Sep. 25, 1978

[30] Foreign Application Priority Data

Sep. 23, 1977 [CH] Switzerland ............. 11624/77

[51] Int. Cl.$^2$ ............................................... B08B 3/02
[52] U.S. Cl. ................................. 134/58 R; 134/173; 134/195; 134/198; 222/94; 239/332; 417/475; 417/478
[58] Field of Search ............... 417/475, 478; 239/331, 239/332; 222/94–96; 134/58 R, 172–174, 195–196, 191, 198

[56] References Cited

U.S. PATENT DOCUMENTS

| | | | |
|---|---|---|---|
| 179,274 | 6/1876 | Cosgrove | 134/174 |
| 686,450 | 11/1901 | Hawkes | 134/196 UX |
| 3,180,418 | 4/1965 | MacLeod | 134/58 R X |
| 3,305,097 | 2/1967 | Natelson | 417/474 X |
| 3,359,916 | 12/1967 | Houston et al. | 417/475 X |
| 4,018,240 | 4/1977 | Palthe | 134/198 X |
| 4,104,005 | 8/1978 | Poirier | 417/478 X |

Primary Examiner—Robert L. Bleutge
Attorney, Agent, or Firm—Craig and Antonelli

[57] ABSTRACT

An apparatus for cleaning a test electrode in process control and chemical engineering. The apparatus includes a storage container from which a cleaning solution is intermittently drawn in by a pneumatically operating peristaltic pump. The pump supplies the cleaning solution to a nozzle which sprays the solution on the electrode.

7 Claims, 3 Drawing Figures

CLEANING APPARATUS FOR TEST ELECTRODES

The present invention relates to a cleaning apparatus and, more particularly, to a cleaning apparatus for test electrodes.

Process control and chemical engineering is often accompanied by considerable difficulties for numerous tasks set in measuring technology. For example, precipitates from solutions to be measured may be deposited on the sensors. The presence of such deposits on the sensors adversely affects the measuring since the short response time required of a sensor is substantially increased and also the danger arises of a so-called memory-effect occurring since the deposit soaks up a certain sample and the change is not detected immediately when the properties of the sensor sample change. Moreover, the presence of such deposits results in an unacceptable falsification of the measured information, especially if the sensor is a constituent of an automatic control system for the automatic control of the system will then make a false correction following a measured value which does not correspond to the actual condition of the sample.

These experiences make it necessary in process control to keep the sensor clean at all times. In contrast to laboratory experiments, the cleaning of the sensor cannot be carried out by manual cleaning and, instead, measures must be taken to allow such cleaning phases to take place completely automatically. For this purpose, a number of different apparatus have been proposed.

In proposed apparatus, the surface of the sensor may be cleaned by mechanically driven wipers or the surface of the sensor may be rubbed over. However, such proposed solutions are completely inadequate with oily or fatty substances since such substances are smeared over the surface of the sensor during the cleaning operation. Consequently, with oily or fatty substances or the like, a cleaning of the sensor can be effected in an ultrasonic field.

In other cases, special cleaning solutions must be provided for removing the deposits from the sensor by flushing or spraying the sensor. The correct cleaning method must always be selected to correspond to the physical and chemical properties of the deposits on the sensor. A thorough survey of methods of cleaning sensors by utilizing cleaning solutions is found in LABO Journal, October 1975, pages 906–911. Moreover, a house journal of the company Dr. Ingold, CH-8902 Urdorf, Switzerland, also mentions various possibilities.

It has been found in the course of extensive operating tests that a number of additional conditions have to be satisfied in a cleaning system utilizing cleaning solutions in addition to the removal of deposits from the sensor or electrode. For example, cleaning solutions may have very corrosive properties and, in other cases, the cleaning mixture may contain organic solvents. In both cases, the materials which the cleaning solution contacts must have quite different properties.

Another important consideration is the risk of explosion in the place where the sensor is employed. In this case, it is only possible to employ a cleaning method which meets the requirements of explosion protection.

Finally, for operating efficiency and reduction in overall costs, an automatic cleaning apparatus must function for at least a year and require no servicing, apart from the charging of cleaning solution into a storage container.

A chemical cleaning solution has been proposed in which a cleaning solution, under pressure, is dispensed by a magnetic valve controlled by a program transmitter. In this proposed system, the valve releases the cleaning solution which is then sprayed by way of a nozzle onto the sensor.

One disadvantage of the last-mentioned cleaning system resides in the fact that the current required for activating the magnetic valve effectively precludes use in an explosive-type arrangement since the presence of an electric current conflicts with the requirements of explosion protection.

Moreover, a further disadvantage resides in the fact that it is difficult to exchange the diaphragm of the magnetic valve and to adapt the diaphragm and magnetic valve to different properties of the cleaning agent.

Furthermore, because of the various cleaning agents and chemical properties thereof, another disadvantage resides in the fact that a plurality of different types of magnetic valves have to be maintained or kept ready.

Yet another disadvantage resides in the fact that the cleaning apparatus itself is exposed to the vapors of the cleaning agent and is thus susceptible to corrosion.

In another proposed cleaning system, a water jet ejector is provided which sucks up the cleaning solution and sprays it onto the sensor. Disadvantages of this system again are the use of an electrically activated magnetic valve which does not provide protection from explosion and the fact that the cleaning solution is diluted by the ejector water and thus becomes less effective.

The aim underlying the present invention essentially resides in providing a cleaning apparatus for test electrodes wherein the test electrodes may be sprayed by a jet of cleaning solution issuing from a nozzle in accordance with a predetermined program.

According to advantageous features of the present invention, the cleaning solution is accommodated in a storage container and is intermittently sucked or drawn from the container by means of a pneumatically operating peristaltic pump and is then ejected at the electrode through a nozzle.

By virtue of the provision of a pneumatically operating peristaltic pump in accordance with the present invention, the pump may be designed in such a way that the electric control circuitry is arranged outside of a region in which lie hazardous components of the cleaning system.

In accordance with the present invention, the pneumatically operating peristaltic pump includes at least two successive deformable tubes arranged in pressure chambers with the volumes of the tubes being compressed by alternate application of super or high pressure to one of the pressure chambers so as to eject the cleaning solution accommodated in the tubes. The tubes are constructed and arranged so as to resume their original shape after the super pressure has been released from the respective pressure chambers, thereby permitting the associated tube to absorb another volume of cleaning solution.

The conveying members of the pneumatically operating peristaltic pump in accordance with the present invention have a large lumina so that there is no danger of blockages at any bottlenecks.

Advantageously, according to the present invention, the possibility exists of producing the parts of the peristaltic pump which convey the chemical solution from a chemically resistant material.

According to a further feature of the present invention, at least one check valve means is provided for controlling a direction of flow of the cleaning solution.

To provide for selective supply of the super pressure to the pressure chambers, according to yet another feature of the present invention, pressure medium conduits or pipes are provided for connecting the pressure chambers to a pressure medium source with an electromagnetic control valve being provided for controlling the flow through the conduits.

According to additional features of the present invention, a programmed transmitter means is provided for controlling the operation of the magnetic control valve.

In accordance with the present invention, the nozzle may be arranged to spray the cleaning solution perpendicularly with respect to the electrode or, in the alternative, may be arranged to spray the cleaning solution at an acute angle with respect to the electrode.

Accordingly, it is an object of the present invention to provide a cleaning apparatus which avoids by simple means the afore-mentioned shortcomings and disadvantages encountered in the prior art.

Another object of the present invention resides in providing a cleaning apparatus in which the cleaning solution is not diluted.

Yet another object of the present invention resides in providing a cleaning apparatus in which the cleaning solution is not carried along by injectors.

A further object of the present invention resides in providing a cleaning apparatus which is simple in construction and, therefore, inexpensive to manufacture.

An additional object of the present invention resides in providing a cleaning apparatus which functions reliably under all operating conditions.

A still further object of the present invention resides in providing a cleaning apparatus which may be safely utilized without requiring extensive explosion protection.

These and other objects, features and advantages of the present invention will become more apparent from the following description when taken in connection with the accompanying drawings which show, for the purposes of illustration only, one embodiment in accordance with the present invention, and wherein.

Figure 1:
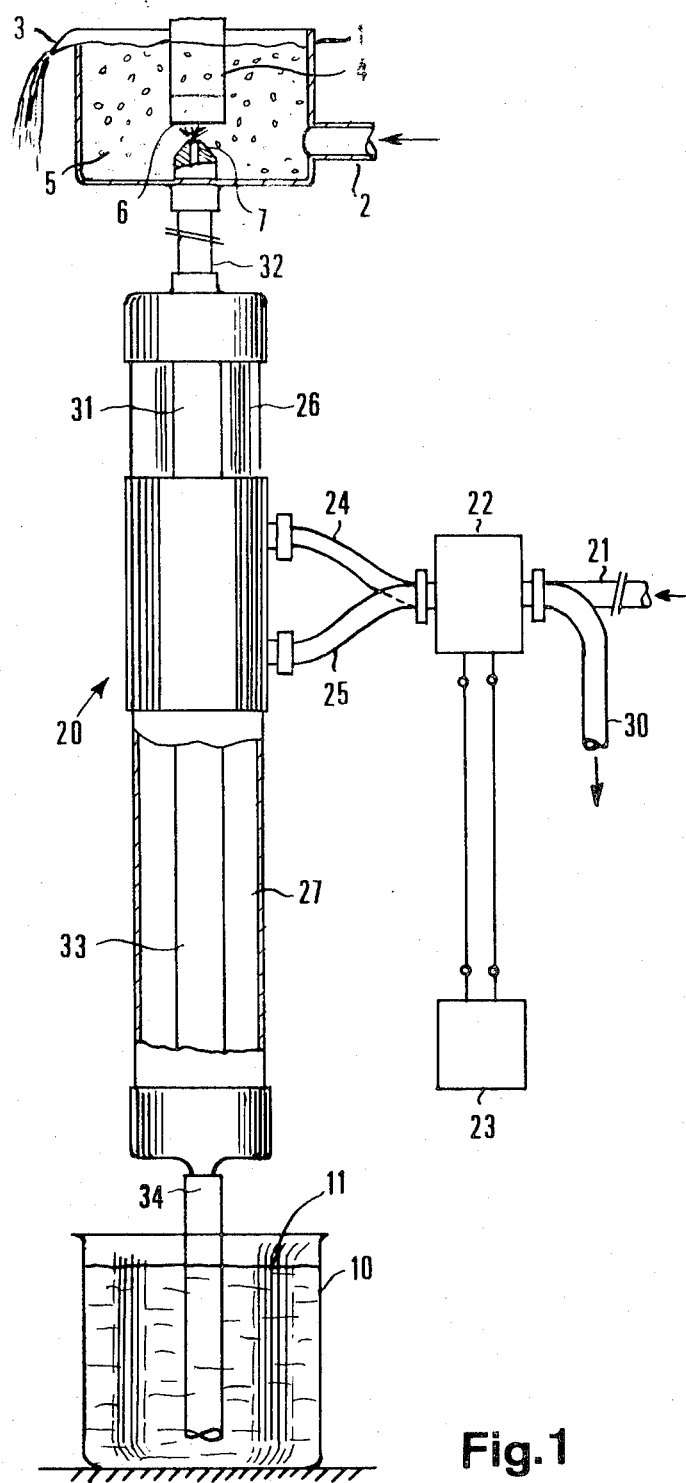
FIG. 1 is a partially schematic view of a complete cleaning apparatus in accordance with the present invention.

Referring now to the drawings wherein like reference numerals are used throughout the various views to designate like parts and, more particularly, to FIG. 1, a vessel 1, having an inlet 2 and an overflow 3, contains a liquid 5 to be analyzed with a sensor 4. The lower end of the sensor 4 is provided with a conventional ion-sensitive electrode 6. The electrode 6 is exposed to the deposition of solids which are contained in the liquid 5. The deposits of the solids have to be removed periodically and automatically without the necessity to remove the sensor 4 from the vessel and without the necessity to clean the same mechanically. For this purpose, a cleaning solution 11, located in a storage container 10, is sprayed on the electrode 6 under pressure from a spray nozzle 7. The spray nozzle 7 is arranged centrally with respect to the vessel 1 or in another suitable position in the vessel 1 so that the spray of the cleaning solution 11 against the electrode 6 results in the deposits being detached, flushed away and then being driven off with the liquid 5 at the overflow 3.

The cleaning solution 11 is periodically sprayed from the nozzle 7 against the electrode 6 by means of a pump generally designated by the reference numeral 20 which is preferably a pneumatically operating peristaltic pump. The pump 20 is controlled by a fluid pressure medium which is applied by a pressure medium conduit 21 and then passes a controllable magnetic valve 22. The magnetic valve 22 is controlled by a programming switch 23 which determines the timed discharge of the pressure medium supply through the pressure medium feed conduits or pipes 24, 25 into various sections of the pump 20.

Figure 2:
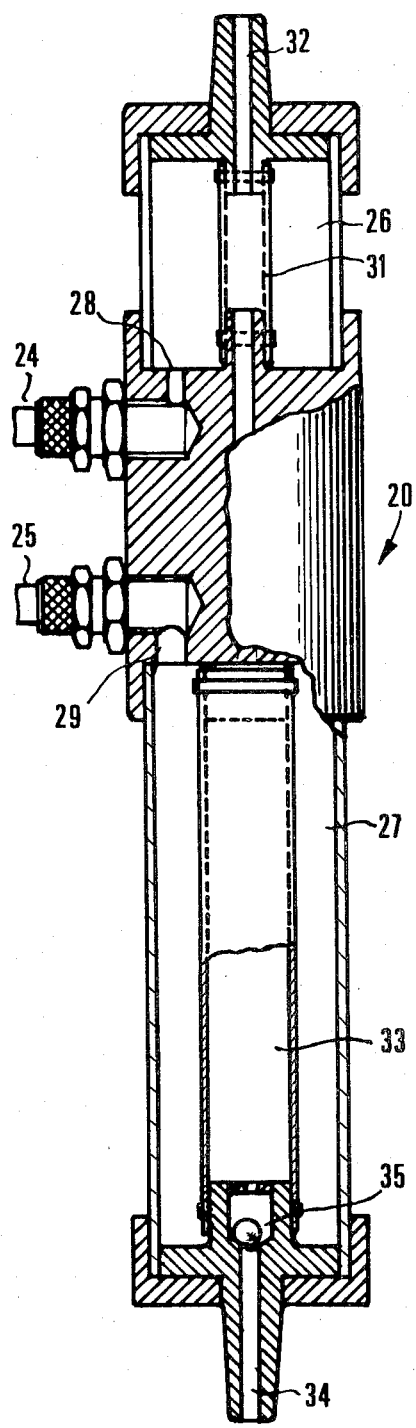
FIg. 2 is a partial cross-sectional view of the peristaltic pump in accordance with the present invention in a rest position.
Figure 3:
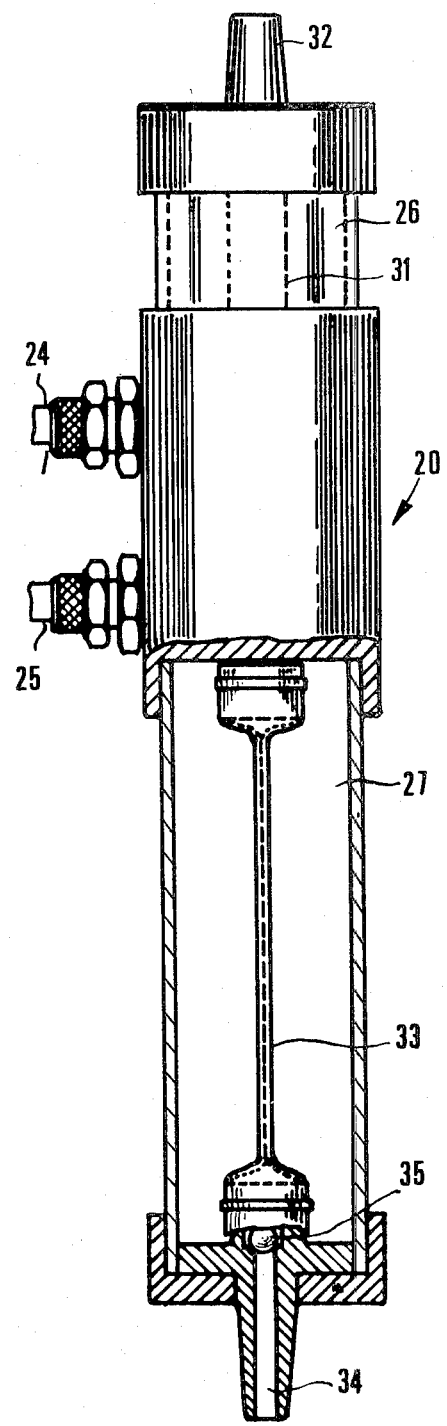
FIG. 3 is a partial cross-sectional view of the pump of FIG. 2 with a compressed pumping or conveying member.

FIGS. 2 and 3 provide illustrations of the method of operation of the pneumatically operating peristaltic pump 20. The pump 20 includes a housing which is divided into an upper pressure chamber 26 and a lower pressure chamber 27. The feed conduit 24 communicates with the upper pressure chamber 26 through a passage 28 and the feed conduit 25 with the lower pressure chamber 27 through a passage 29.

The magnetic valve 22 operates in such a way that the pressure medium is fed through the feed pipe 24 into the upper pressure chamber 26 during a first operational phase. A flexible tube 31 is compressed in the first operational phase so as to seal an outlet opening 32. The next operational phase involves the changeover of the pressure medium supply through the feed conduit 25 to the lower pressure chamber 27. A flexible tube 33 contained in the lower pressure chamber 27 is thus compressed (FIG. 3) and the contents of the tube 33 are driven out. The upper pressure chamber 26 is simultaneously vented through an exhaust 30 (FIG. 1) so that the flexible tube 31 assumes its original shape and thus releases the outlet opening 32. The contents of the tube 33 can, therefore, escape through the outlet opening 32.

A check valve, which closes in a known manner when a super or high pressure occurs in the tube 33, is provided in order to prevent the contents of the tube 33 from issuing downwardly through a suction opening 34. If the pressure is then exhausted from the lower pressure chamber 27 through the magnetic valve 22 and exhaust 30, the tube 33 widens to its normal shape (FIG. 2) and therefor sucks the cleaning solution 11 from the container 10 through the suction opening 34. The check valve therefor releases the passage or suction opening 34 in the direction of suction. The upper pressure chamber 26 is placed under pressure in this operational phase so that the flexible tube 31 is compressed and once again seals the outlet opening 32. A backflow cannot occur during suction and the cleaning solution is invariably conveyed from the container 10 toward the outlet opening 32 or to the nozzle 7.

Since the length of the feed conduits 24, 25 is not restricted, the magnetic valve 22 and the program control means 23 can be arranged at a place where possible switching sparks cannot ignite explosive vapors. As the magnetic valve 22 additionally has to control only neutral pressure medium, for example, air, the risk of explosion is eliminated.

The pump 20 allows a flow of liquid in a straight line and operates with relatively large lumina in the feed pipes, delivery pipes and the actual pump members. The possibility of the pump components being blocked by foreign bodies is, therefore, extremely slight.

By suitable choice of the material for the components which come into contact with the cleaning solution 11 in the pump 20 and, in particular, of the flexible tubes 31, 32, it is possible for the pump 20 to be used for the most varied types of cleaning solution without having to exchange components or without having to keep different types of pumps available.

Moreover, the pump 20 of the present invention has the advantage over a mechanically operated peristaltic pump in that the tubes 31, 33 are not mechanically stressed by plungers or other pressure members and that the contents of the tube 33 are quickly ejected by the action of the pressure on the full tube surface so that the jet issuing from the nozzle 7 is at a high speed, whereby intensive cleaning of the electrode 6 is readily achieved.

While we have shown and described only one embodiment in accordance with the present invention, it is understood that the same is not limited thereto, but is susceptible of numerous changes and modifications as known to one having ordinary skill in the art, and we therefor do not wish to be restricted to the details shown and described herein, but intend to cover all such changes and modifications as are encompassed by the scope of the appended claims.

We claim:

1. A cleaning apparatus for test electrodes disposed in a vessel containing a solution to be analyzed by the test electrodes in which the test electrodes are adapted to be sprayed by a jet of cleaning solution issuing from a nozzle in accordance with a predetermined program, the cleaning apparatus comprising:

a pneumatically operating peristaltic pump means operatively connected with the nozzle for intermittently drawing the cleaning solution from a storage container and for ejecting the cleaning solution through the nozzle against the test electrodes so as to remove deposits of solids therefrom while the test electrodes remain in the solution.

2. A cleaning apparatus according to claim 1, wherein the pneumatically operating peristaltic pump means comprises at least an upper and lower pressure chamber, at least two sequentially arranged deformable tubes for accommodating a volume of cleaning solution arranged in the pressure chambers, the tubes being adapted to be compressed by an alternate application of a high pressure to one of the pressure chambers so as to eject the cleaning solution from the deformable tubes, the deformable tubes being adapted to resume an original shape after the high pressure has been released from the respective pressure chambers so as to permit the tubes to draw in a volume of cleaning solution.

3. A cleaning apparatus according to claim 2, wherein at least one check valve means is provided for controlling a direction of flow of the cleaning solution.

4. A cleaning apparatus according to claim 3, wherein a magnetic valve means is provided for controlling a flow of pressure medium to the respective pressure chambers, pressure medium conduits are arranged between the magnetic valve means and the respective chambers and between a pressure medium source and the magnetic valve means.

5. A cleaning apparatus according to claim 4, wherein a program transmitter means is provided for controlling an operation of the magnetic valve means.

6. A cleaning apparatus according to one of claims 1, 2, 3, 4, or 5, wherein the nozzle is mounted at the vessel so as to spray the cleaning solution perpendicularly onto the test electrode.

7. A cleaning apparatus according to one of claims 1, 2, 3, 4, or 5, wherein the nozzle is mounted at the vessel so as to spray the cleaning solution against the test electrode at an acute angle.

* * * * *